(12) United States Patent
Bourhis et al.

(10) Patent No.: US 6,723,712 B2
(45) Date of Patent: Apr. 20, 2004

(54) ANTIVIRAL AGENT FOR USE IN TREATMENT OF CANCER

(75) Inventors: Jean Bourhis, Sceaux (FR); Bassam Abdulkarim, Vanves (FR); Eric Deutsch, Paris (FR)

(73) Assignees: Institut Gustave Roussy, Villejuif Cedex (FR); Universite Paris-SUD XI, Orsay Cedex (FR)

( * ) Notice: Subject to any disclaimer, the term of this patent is extended or adjusted under 35 U.S.C. 154(b) by 0 days.

(21) Appl. No.: 10/138,999

(22) Filed: May 2, 2002

(65) Prior Publication Data

US 2002/0193339 A1 Dec. 19, 2002

Related U.S. Application Data

(63) Continuation of application No. PCT/EP00/11246, filed on Nov. 3, 2000.

(30) Foreign Application Priority Data

Nov. 4, 1999 (EP) .............................................. 99402748

(51) Int. Cl.[7] .............................................. A61N 3/675
(52) U.S. Cl. ...................................................... 514/86
(58) Field of Search ............................................ 814/86

(56) References Cited

PUBLICATIONS

Abdulkarim et al., Oncogene, (Apr. 4, 2002, 21/15 (2334–2346), 64 references(s) Abstract Only.*
See–Lasley et al., Manual of Oncology therapeutics, C.V.Mosby Co., St. Louis, 1981, p. 88 and 104.*
Neyts, J. et al., "The Antiviral Agent Cidofovir [(S)–1–(3–Hydroxy–2–phosphonyl–methoxypropyl) Cytosine] Has Pronounced Activity against Nasopharyngeal Carcinoma Grown in Nude Mice", *Cancer Research*, 58(3):384–388 (Feb. 1, 1998).
Snoeck, R. et al., "Effect of Cidofovir on the Tumor Growth of SiHa (Human Cervical Carcinoma) Cells in Nude Mice", *Antiviral Research*, 34(2):A69 (1997) Meeting Info: Meeting of the International Society for Antiviral Research and the Tenth International Conference on Antiviral Research Atlanta, Georgia, USA (Apr. 6–11, 1997) (Abstract only).
De Clercq, E. et al.,. "Antitumor Potential of Acyclic Nucleoside Phosphonates", *Nucleosides & Nucleotides*, 18(4&5):759–771 (1999) (Abstract).
Reynolds, "Martindale The Extra Pharmacopoeia", Royal Pharmaceutical Society, London, GB XP002133250, pp. 651–652 (1996) (Abstract).
Reynolds, "Martindale The Extra Pharmacopoeia", Royal Pharmaceutical Society, London, GB XP002133251, pp. 664–667 (1996) (Abstract).
Reynolds, "Martindale The Extra Pharmacopoeia", Royal Pharmaceutical Society, London, GB XP002133252, pp. 653–657 (1996) (Abstract).
Copy of International Search Report dated Feb. 2, 2001.
Abdulkarim, B. et al., "Antiviral agent Cidofovir decreases Epstein–Barr virus (EBV) oncoproteins and enhances the radiosensitivity in EBV–related malignancies", *Oncogene*, 22:2260–2271 (2003).
Abdulkarim, B. et al., "Antiviral approaches for cancers related to Epstein–Barr virus and human papillomavirus", *The Lancet Oncology*, 2:622–630 (Oct. 2001).
Abdulkarim, B. et al., Antiviral agent Cidofovir restores p53 function and enhances the radiosensitivity in HPV–associated cancers, *Oncogene*, 21:2334–2346 (2002).

\* cited by examiner

*Primary Examiner*—Jerome D. Goldberg
(74) *Attorney, Agent, or Firm*—Merchant & Gould P.C.

(57) ABSTRACT

The invention relates to an antiviral agent for use in combination with an anticancer agent, for the treatment of cancer. Especially, the invention provides means for the treatment of non-virus-associated cancer.

7 Claims, 11 Drawing Sheets

ANTIVIRAL AGENT FOR USE IN TREATMENT OF CANCER

Figure 1A:
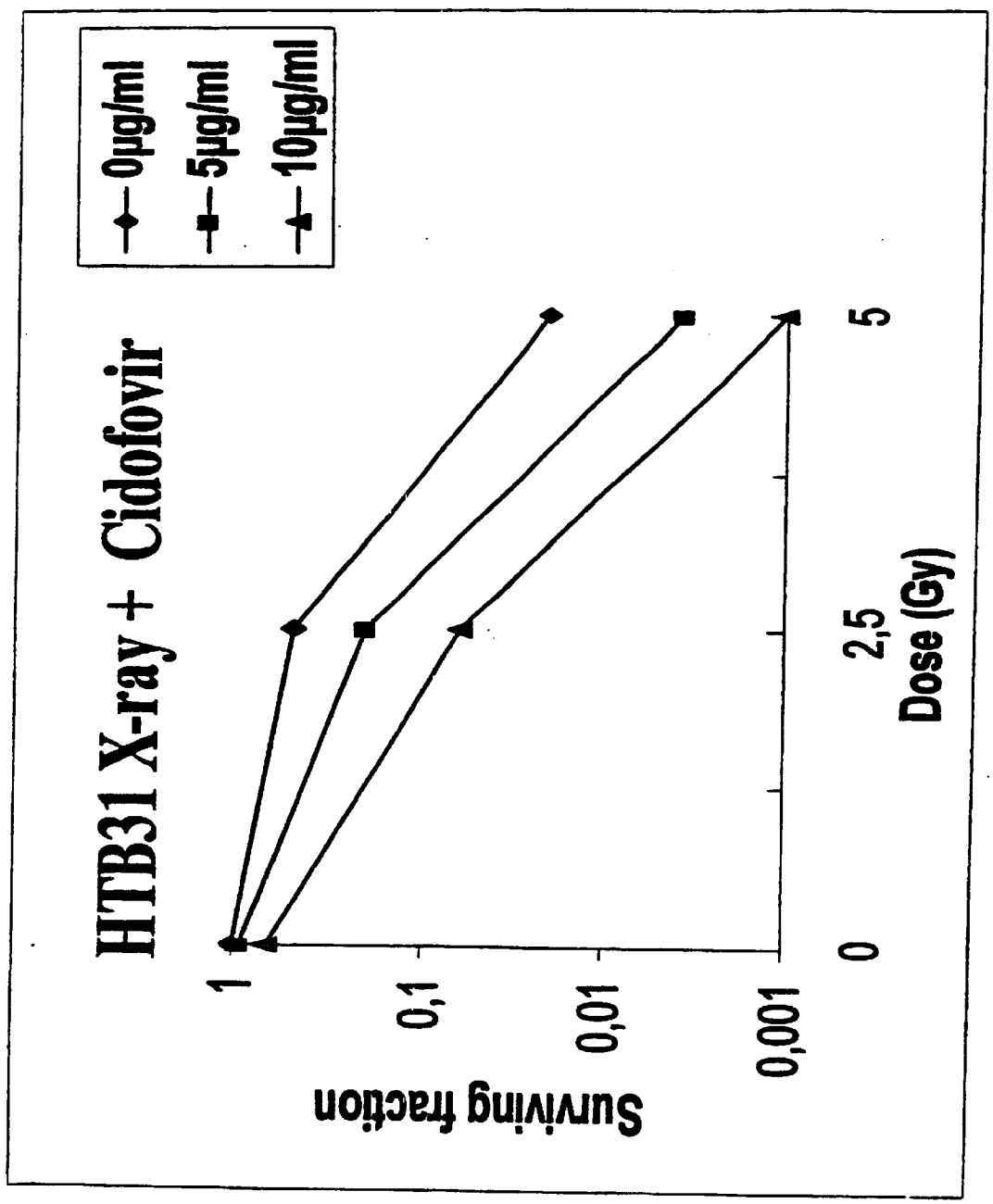

This application is a continuation of international application number PCT/EP00/1246, filed Nov. 3, 2000, pending.

The present invention relates to the field of the treatment of cancer and especially involves the use of antiviral agents for the treatment of cancer. The invention relates to the treatment of virus-associated cancer, or non-virus-associated cancer.

In studying various human tumor cell lines derived from virus-associated cancers, the inventors have shown that antiviral agents used in combination with other therapeutic agents, may provide a new way for the treatment of cancer, with improved sucess in controlling the development of the tumor. The inventors have also shown that said combination of an antiviral agent with another therapeutic agent may also be used advantageously in the treatment of non virus-associated cancers.

Although there has been no direct relationship established between a detected viral infection and the occurrence of cancer in human, studies have shown in the past that virus infection can be a co-factor frequently associated with carcigonenesis in infected cells and as a consequence can be linked to the development of malignant lesion and in general related with the development of cancer.

In these situations where an infection by a virus can be correlated with the development of malignancy especially in the human body, it is believed that other contributing factors may also be involved.

To date, it appears that human cancers, associated with virus infection are mainly represented by lymphomas and carcinomas. For example, infection by the Epstein-Barr virus (EBV) has been detected in nasopharyngeal carcinomas, Burkitt and other lymphomas, papillomavirus infection (HPV) has been shown to be involved in some head and neck carcinomas, and uterine cervix carcinomas, infections by Hepatitis B or C viruses have been associated with the occurrence of hepatocarcinomas.

These virus-associated cancers, where viral infection is a co-factor involved in the carcinogenesis of human cancer represent 15 to 20% of the whole number of cancers in the world (26,27).

From a general point of view, cancers, including virus-associated cancers, are treated through different ways. It is especially well-known that cancer treatment comprises surgery, radiation and chemotherapy. More recently immunotherapy has been introduced as a further available treatment regimen. It is also noted that cancers may be treated, if appropriate, with a combination of several of these available treatments. Therefore, the above-cited treatment regimens can be viewed as constituting a primary therapy or depending upon the specific cases, as an adjudant therapy.

As far as virus-associated cancers are concerned, it is noted that conventional treatments of the type of the above-cited treatment, have shown a relatively high level of failure to cure or improve the situation of the patients, especially in locally advanced disease (40–60% failure in stage III–IV nasopharyngeal carcinoma and in stage III carcinoma of the uterine cervix (27)).

Therefore, new approaches for therapeutic treatment of cancers are desirable. Such an alternative or complementary possibility of treatment of cancers is provided by the inventors through the definition of means involving the use of antiviral agents.

Interestingly, the efficiency which has been observed by the inventors on the control of tumors associated with viral infection, when using antiviral agents, has also been shown unexpectedly on non virus-associated cancers.

In a publication (1), Andrei G. et al (<<Inhibiting Effect of Cydofovir (HPMPC) on the Growth of the Human Cervical Carcinoma (SiHa) Xenografts in Athymic Nude Mice>>), have disclosed that in view of a strong association noticed between infection with specific genital viruses (HPV viruses) and the development of cervical cancer, an assay was made, to treat cell lines derived from human cervical carcinoma with HPMPC ([(S)-1-[3-hydroxy-2-(phosphonomatoxy)propyl]cytosine, Cidofovir) which is known to be an antiviral agent.

As a result of this experimental work, Andrei et al (1) have shown that cell proliferation of these cell lines was inhibited in a concentration-dependent and in a time-dependent fashion. They further report that effects of HPMPC on the growth of cervical carcinoma xenografts in athymic nude mice has been observed, allowing to conclude that animals that were injected intratumorally with HPMPC at a certain dose, have shown statistically significant reduction in tumor size compared to a placebo group or to a group of animals treated with another specific antiviral agent. They further state that, when HPMPC was administered topically or systemically, no reduction of tumor growth was observed when nontoxic concentrations of the compound were used.

Within the frame of the present invention, the inventors have observed that contrary to what has been concluded by Andrei et al in the above-cited publication, HPMPC, among other antiviral agents, can be used for the treatment of cancer and especially by using non toxic systemic concentrations. Both virus-associated cancers and non virus-associated cancers may be treated by the use of antiviral agent in appropriate conditions defined in the present invention.

The inventors provide means for the treatment of cancer, that comprise the use of antiviral agents in combination with known groups of anticancer agents, said combination enabling a synergic effect to occur between the antiviral agent and the anticancer agent. It is stated that anticancer agents implicated in the production of this synergic effect include conventional anticancer agents among those used for the anticancer conventional therapy cited hereabove.

The present invention therefore relates to a method of treatment of cancer, which comprises the steps of:
administering to a patent in need thereof an anticancer agent and
administering to said patient an antiviral agent.

Each of the features described hereafter for the definition of the type of cancer to be treated or in relation to the nature or use of the anticancer agent or of the antiviral agent is applicable for the implementation of said method of treatment.

The sequences of administration of said anticancer and said antiviral agents are defined by the skilled person.

According to the invention, the expression <<synergic effect>> signifies that the effect obtained with the combination of several agents within the scope of the invention is higher than the effect which is obtained with only one of these agents or, advantageously the effect which is obtained with the combination of the above said agents is higher than the addition of the effects obtained with each of these agents used separately.

Accordingly, the inventors have shown that antiviral agents can be used in combination with other groups of molecules, compositions, or irradiation treatments used as anti-cancer agents for the treatment of cancer, and especially for the treatment of virus-associated cancers, thereby producing an improved effect on the tumor development.

In the present invention, the expression <<antiviral agents>> relates to agents having an interaction effect and for instance an inhibitory effect on the infection of cells by a virus. Within the possible effects of said antiviral agents, one may include the capacity of the antiviral agent to inhibit the infection of the host cells by the virus and/or to inhibit the replication of the virus or the proliferation of the virus in host cells. Additionally or alternatively, the antiviral agents of the invention are agents which can have a direct effect on the infected host cells including for instance against their transformation towards a malignant state.

For the purpose of the invention, an antiviral agent which appears to produce a result in the treatment of cancer, when combined with an anticancer agent as defined hereafter, is designated as an antiviral agent.

By the expression <<anticancer agent>> is meant according to the present invention, any known agent or agent to be developed which has, in proper conditions, an activity on the formation of a malignant lesion and/or on the growth or on the spreading of the formed malignant lesion towards the formation, growth and spreading of the tumor.

In other words, it is pointed out that, according to the invention, an anticancer agent can interfere with the process of malignant transformation of a normal cell and/or with the development or spreading of the tumor. In some cancers, anticancer agents can interfere with abnormal cell differenciation or metastases.

It is also emphasized that, the definition of the anticancer agent applies to agents having effects on the control of the biologic and/or biochemical basis for cancer disease, or on the control of the clinical progress of the disease or recurrence thereof. In a particular embodiment, the anticancer agent is able to cure the cancer disease.

The expression <<treatment of cancer>> according to the invention, can be construed as encompassing the effect that is normally sought with an anticancer agent, as defined above. Advantageously, it encompasses the effect which can be obtained on malignant cells or on developed tumors, following administration of the combination of the antiviral-agent and the anticancer agent. Especially it encompasses reduction in tumor size, which can be measured in accordance with the assays provided in the examples of this patent application.

The word <<combination>> which is used according to the invention, designates the use of the antiviral agent and of the anticancer agent in the treatment of a detected cancer either a virus-associated cancer or a non virus-associated cancer. In a particular embodiment of the invention, it encompasses the associated use of both agents if they can be used together, for instance in the same composition. Alternatively, it designates the separated administration of these agents. Said <<separated>> administration includes the simultaneous, concomitant or sequential administration in time, either as a consequence of the difference in physical or chemical nature of the agents or as a result of the regimen or schedule of treatment requiring that the agent be used separately in time, or be used through separated routes of administration.

Antiviral agents or anticancer agents are as a consequence proposed for use in treatment of cancer, when they are capable, in combination, to produce an interaction effect on the occurrence or on the development of a malignant lesion and/or on the occurrence or on the development of the resulting tumor.

According to a particular embodiment, the invention relates to the use of an antiviral agent replying to one or several of the various definitions provided in the present application, for the manufacture of a drug for the treatment of a cancer either of a virus-associated cancer or of a non-virus-associated cancer, wherein said drug is used in combination with an anti-cancer agent.

The invention also relates to the use of an antiviral agent for the manufacture of a drug suitable for the treatment by systemic route of a cancer, in accordance with the above-given definitions.

Accordingly, in a particular embodiment, the invention relates to a method for the treatment of cancer comprising the steps of administering an antiviral agent through the systemic route, to a patient in need thereof, administering to said patient, an anticancer agent.

Depending on its nature and properties, the anticancer agent can also be administered through the systemic route. Alternatively, it can be provided to the patient through another route, especially locally.

Among the antiviral agents which can be used according to the invention, antiviral agents which are non-specific for a particular virus or for a determined group of viruses, are of particular interest.

In a particular embodiment, the invention relates to an antiviral agent as defined according to the invention, for use in appropriate conditions, wherein this agent is chosen among compounds or compositions having a broad spectrum antiviral activity.

Antiviral agents may be classified in several groups which may sometimes overlap, depending on the parameters which are used for the classification.

The specificity of the antiviral agent with respect to a particular type of virus, or to the contrary with regard to its activity against a broad spectrum of viruses, may be one of the possibilities of classification of these agents.

It is also noted in accordance with the invention, that the antiviral agents can be chosen with respect to their capacity to interact with the targeted virus or with the host cells, especially when the treated cancer is associated with viral infection.

In a particular embodiment, the invention relates to an antiviral agent replying to one or several aspects of the definitions given above, for use in the treatment of cancer, wherein this antiviral agent has a cytotoxic activity on the cells infected by the virus.

In addition or alternatively, the antiviral agent used in accordance with the present invention is an antiviral agent capable of inhibiting viral polymerases and/or cellular polymerases.

Advantageously, the invention proposes the use of antiviral agents for the treatment of cancer, wherein the agent has an activity on the cell cycle regulation of tumor cells. For instance, this activity is observed as an action against the pathway involving cyclins; preferably the antiviral agent interferes with cyclin A in the tumor cells. The antiviral agents capable of interfering with the cyclins' pathway are advantageously selected among those which reply to one or several of any of the characteristics which are disclosed in the present patent application.

In a preferred embodiment of the invention, the antiviral agent which is used is a nucleoside analogue and in a particular embodiment, it is an acyclic nucleoside phosphonate analogue.

According to a preferred embodiment, the acyclic analogues of nucleosides are substituted-N-alkyl derivatives of heterocyclic basis, in which the nucleoside sugar moiety is replaced by a substituted carbon chain bearing hydroxy groups. Once administered to an organism, the biologically active nucleoside analogues usually modify and give rise to production of 5' monophosphates, active in vivo.

Preferred antiviral agents concerned by the invention are acyclic nucleoside phosphonate analogues. It is pointed out that said acyclic nucleoside phophonate analogues, are characterized in that their predominant activity is due to DNA polymerase inhibition. Advantageously, in accordance with the invention, they are not dependent upon the presence of a viral tyrosine kinase for their activity. A number of these nucleotide analogues have been synthesized and evaluated both in vitro and in vivo. Examples of these are the [3-hydroxy-2-phosphonylmethoxypropyl] derivatives of adenine (HPMPA) or cytosine (HPMPC, cidofovir), cyclic HPMPC (cHPMPC), 9-(2-[phosphonylmethoxyethyl] derivatives of adenine (PMEA, adefovir) or guanine (PMEG), 2-6 diaminopurine (PMEDAP), cyclo-propyl PMEDAP (cPr-PMEDAP) and related compounds with similar activities (29).

The inventors have obtained particularly interesting results in using HPMPC [(S)-1-[3-hydroxy-2-(phosphonomethoxy)propyl]cytosine] (designated Cidofovir®). This antiviral agent has been extensively disclosed in European patent 0 253 412.

These anti-viral agents have a predominant mode of action that is targeted at viral and cellular DNA. Their activity is mainly directed to the viral DNA, although not selectively since they have also cellular effects leading to cytotoxicity, especially at concentrations much higher than those needed for the viral inhibition.

One of the predominant mechanisms involved in the anti-viral effect of the nucleoside phosphonate analogues is the inhibition of the viral DNA polymerase, at a concentration generally 10 to 1000 lower than that needed to inhibit the cellular DNA polymerases alpha, beta, delta and hence cellular proliferation (28,29).

The inventors have also shown that the enhanced tumor radiosensitivity observed when combining the administration of radiotherapy with a treatment with an antiviral agent can be associated in several human virus-related cancers, with a down regulation of some viral oncoproteins and with an increase of radiation-induced apoptosis.

The above disclosed elements relating to the biological pathways explaining the antiviral activity, shall not be construed as providing limitation regarding the activity which is required especially to enable the interaction of the antiviral agent, with the virus or with the host cells. To the contrary, any antiviral agent showing an activity in the treatment of cancer through another biological pathway could be used, provided a result is obtained in cancer treatment.

In a particular and preferred embodiment, the antiviral agent of the invention is used in combination with an anticancer agent comprising administration of radiotherapy. The antiviral agent is advantageously Cidofovir used in combination with a treatment of radiotherapy.

The inventors have indeed observed that the association of an antiviral agent and of radiation therapy against tumors including against virus-associated tumors or non virus-associated tumors, enables a synergic effect to occur thereby remarkably improving the likelihood of success of treatment and moreover enabling the antiviral agent to be used in accordance with treatment modalities which were presented in the prior art as unacceptable for the systemic route of cancer treatment.

As a matter of fact, the inventors have shown that doses of antiviral agents which are lower than doses which were assayed in the prior art to try to obtain a therapeutic effect, can be used in accordance with the invention, enabling to obtain an unexpected effect with respect to the result which would have been obtained, in cumulating the effects of the individual administration of the antiviral agent with the same dose on the one hand or of the anticancer agent on the other hand.

Therefore, antiviral agents which would have been disregarded for the treatment of cancer especially by the systemic route of treatment, because the doses which would have been required to obtain a therapeutic effect was not admissible in terms of toxicity, in view of the results disclosed in the prior art have been shown to present an interest in accordance with the present invention, when used in combination with another anticancer agent.

Especially the combined use of these antiviral agents with anticancer agents such as radiation, provides an effect on tumors or on malignant cells, resulting from cooperation of both agents and in the absence of occurrence of toxic effects, thereby becoming suitable agents for the treatment of cancer, either of virus-associated cancer or of virus-associated cancer.

The synergic effect has especially been shown on tumors which presented poor reactions when treated by radiation only, or by the antiviral agent alone, including when intratumoral administration of the antiviral agents had no effect or a poor effect on the tumor growth.

The inventors have shown to the contrary that the combination of the antiviral agent and of radiation induces or enables a significant effect on the growth of the tumor, even enabling the complete remission of the tumor for a period of time over fourty days.

This effect has been shown in the context of the invention, either after intratumoral administration of the antiviral agent or after subcutaneous administration of said agent. In this latter case, the doses which can be administered were lower than doses which were disclosed in the prior art, as toxic for the organism.

In order to illustrate the possible conditions for the treatment, it is indicated that for an anticancer agent that would be radiotherapy doses comprised within the range of 40 to 70 Gy can be used and for an antiviral agent that would be Cidofovir doses of the order of 1 to 100 mg/kg may be envisaged in human.

According to another embodiment of the present invention, the antiviral agent is proposed for use in the treatment of cancer, either for the treatment of virus-associated cancer, or for the treatment of non-virus-associated cancer, in combination with an anti-cancer chemotherapeutic agent. This anticancer agent can be chosen in the group of well-known chemotherapeutic agents used in the treatment of cancer, independently of the association of the treated cancer with any virus infection. As an example, cisplatine and etoposide are for instance cited. Treatments involving the use of cytokines are also concerned.

According to another embodiment, the invention provides for an antiviral agent and its use in the treatment of virus-associated cancer wherein the antiviral agent is used in combination with an anticancer immunotherapeutic agent.

It is noted that the conventional treatment available for cancer, independently of presence or absence of an associated-virus can be also combined, and especially both radiation, chemotherapeutic and/or immunotherapeutic agents can be used in addition to the treatment by the antiviral agent.

The antiviral agent which is used according to the invention for the treatment of virus-associated cancer or of non-virus-associated cancer or for the manufacture of a drug for said treatment can be used either through systemic, intratumoral or topical routes, and therefore can be formulated according to the appropriate way depending upon the administration route.

Parenteral administration is preferred including intravenous, intradermal, intramuscular, intrathecal, and other parenteral administration routes.

The invention also relates to compositions comprising an antiviral agent which are suitable for administration to the human body comprises the use of antiviral agent at doses which are not toxic for the organism when administered by systemic route and especially which are capable of producing the effect sought. These doses are determined in accordance with the usual practice in this field.

Such a composition of the invention is appropriate for the treatment of cancer, in particular for the treatment of cancer in a human patient, and in a particular embodiment when combined with the use of another treatment protocol including radiation, chemotherapy and immunotherapy.

Based on the above given definitions, the invention provides compositions comprising an antiviral agent, said compositions being adapted for use in a treatment of cancer, in combination with anticancer agents.

Where the antiviral and anticancer agents are both chemotherapeutic substances, they may be associated in kits, if appropriate.

Other features of the invention and advantages of the use of antiviral agents in accordance with the invention are provided in the following examples.

When a virus is associated with the occurrence of the cancer requiring therapeutic treatment, it can be in particular a target of the treatment as DNA virus.

Within the group of cancers associated with infection by DNA viruses, the invention relates to the treatment of virus-associated cancers wherein the occurrence of the cancer is linked with the infection by a virus chosen among Herpes viruses, Adenoviruses (21), Polyoma viruses, Papillomaviruses (HPV)(2,3, 4, 9, 10, 20, 22), Epstein-Barr viruses (5, 15,23), Hepatitis DNA viruses (HBV or HCV).

In the above paragraphs, some specific cancers have been cited which are known to be associated with infection by particular viruses or virus strains.

The invention especially concerns the use of antiviral agents in the above and following described conditions in the treatment of HPV-associated cancers, EBV-associated cancers or HBV-associated cancers, HCV-associated cancers.

It is emphasized that the effect which is sought in using antiviral agents for the treatment of virus-associated cancers is not dependent upon the cellular type of the malignant cells or dependent upon the tumor and unexpectedly is efficient even in the absence or virus.

The invention also relates to the association, for example in a kit, of an antiviral agent and of an anticancer agent.

Said antiviral agent and said anticancer agent can be used, depending upon their nature, either together, including in the same composition for administration to the patient, or can be physically separated for simultaneous or concomitant use. Alternatively, the antiviral agent and the anticancer agent can be used sequentially during the administration of the treatment.

LEGEND TO FIGURES

Figure 1B:
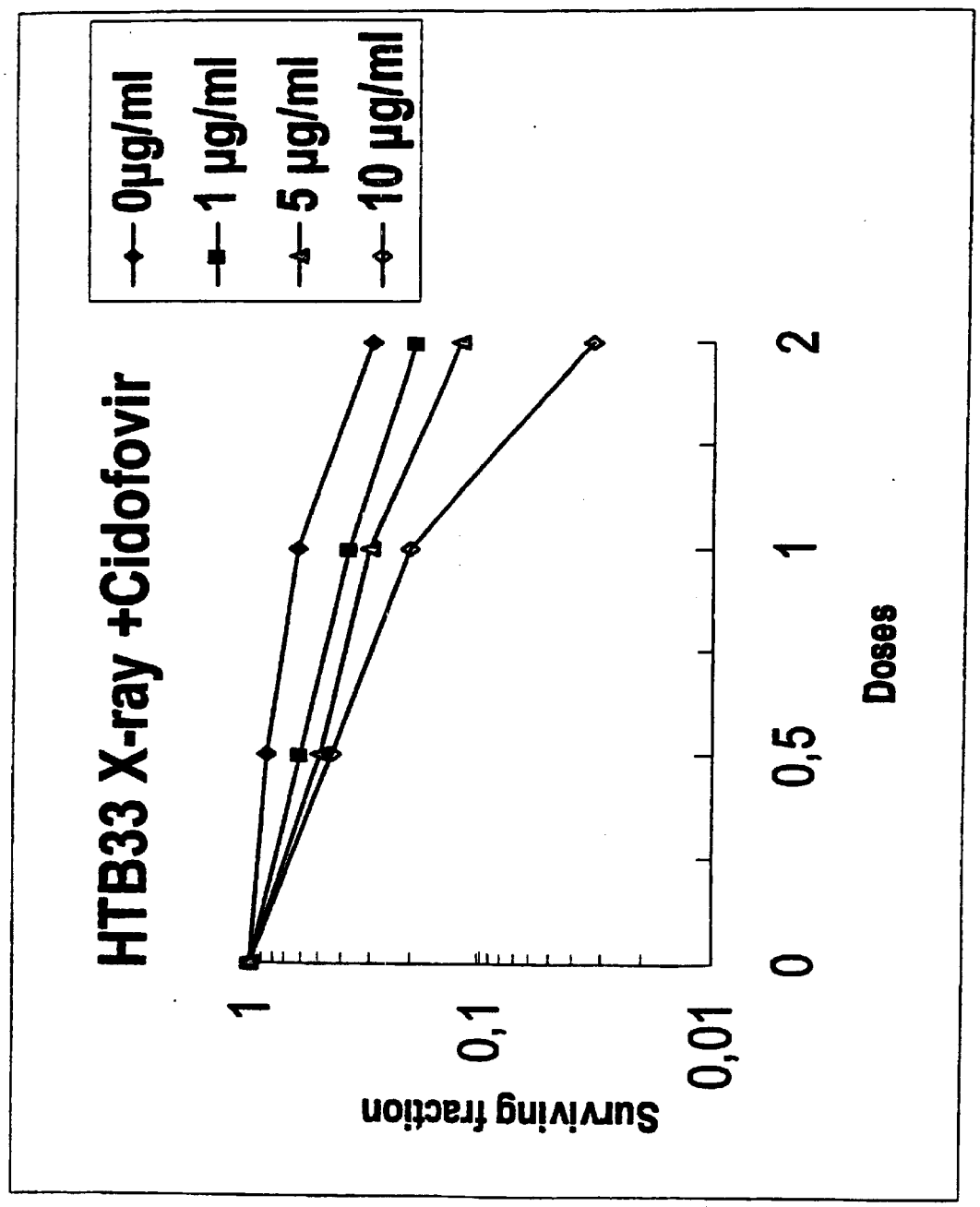
Figure 1C:
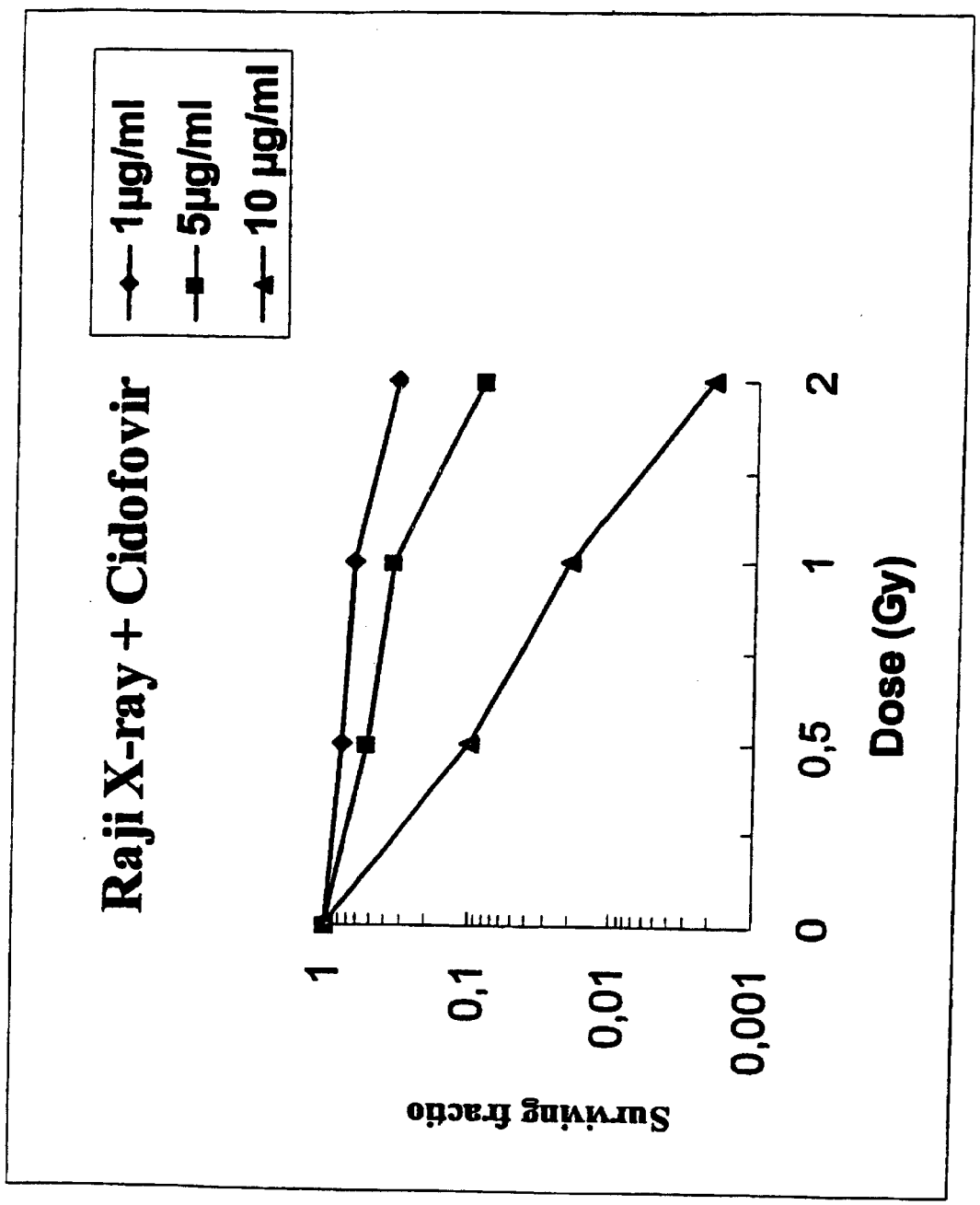
Figure 2A:
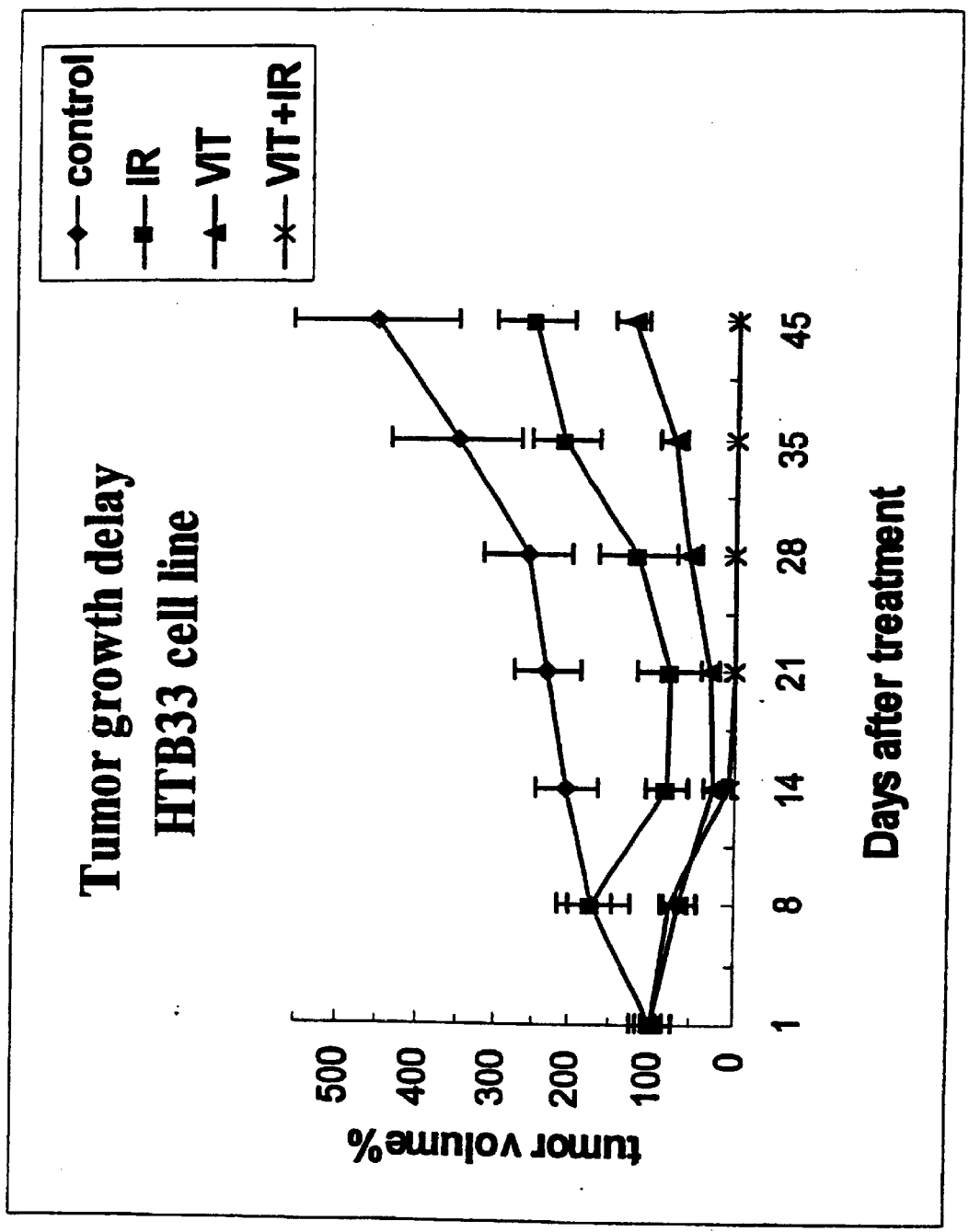
Figure 2B:
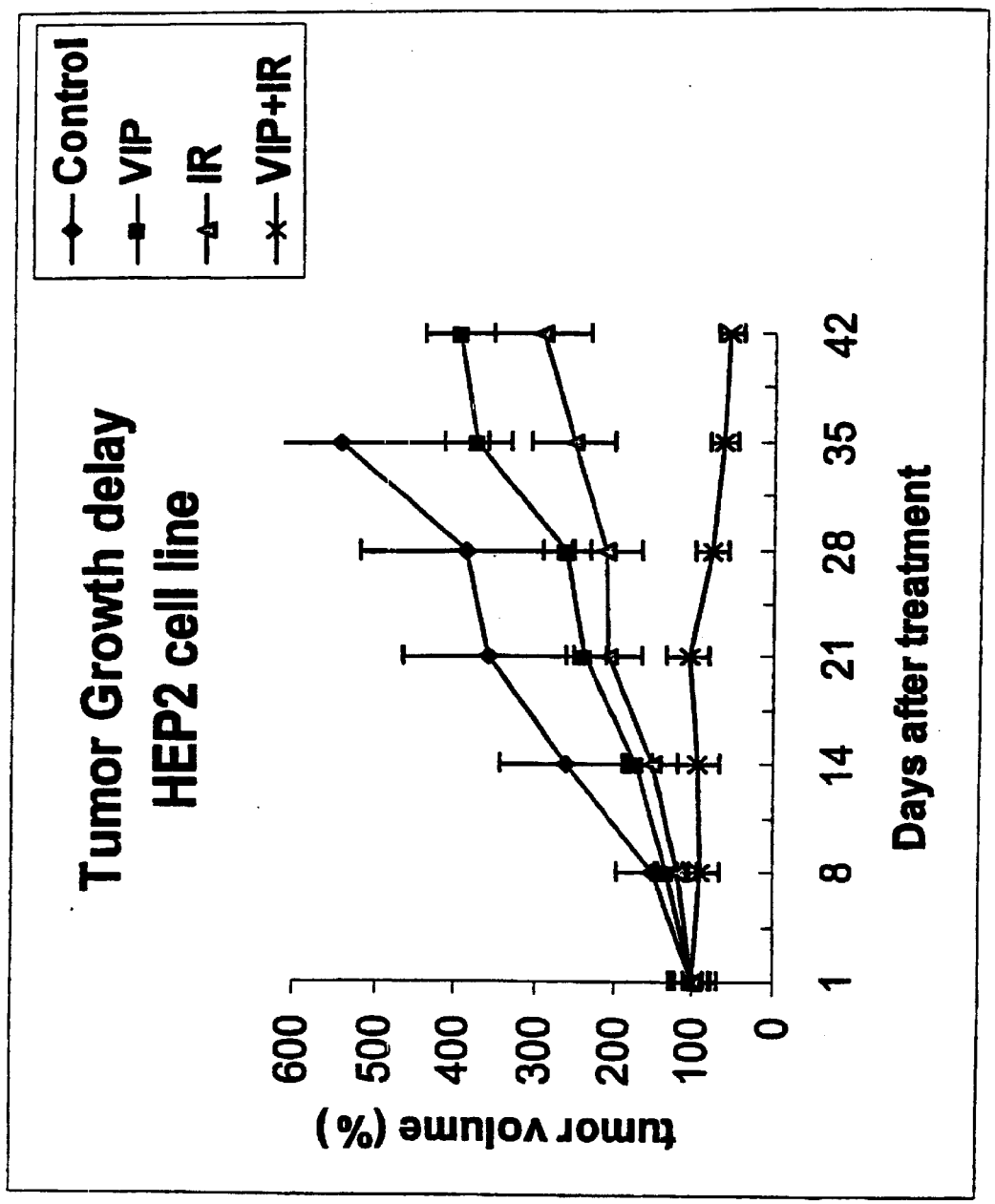
Figure 2C:
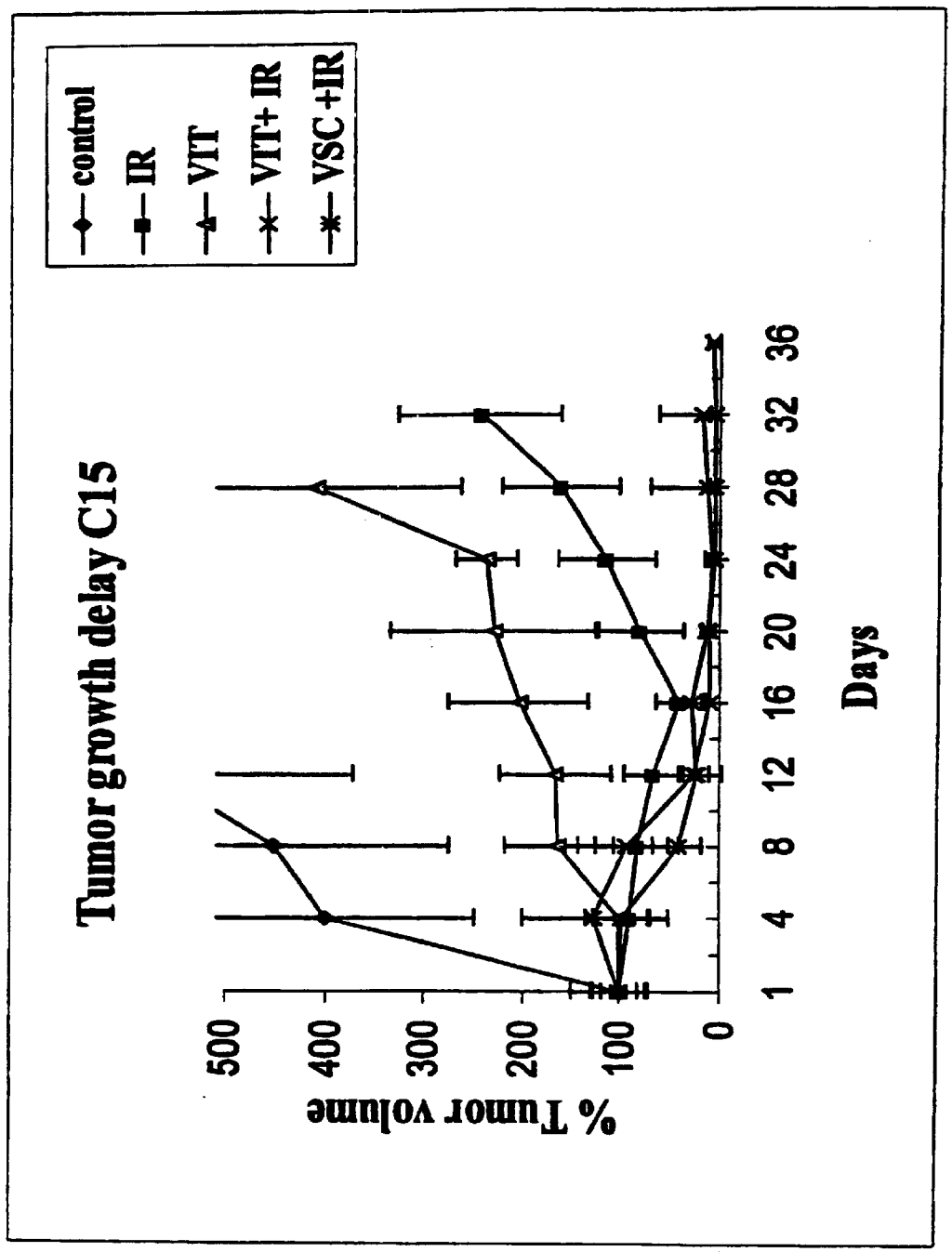
Figure 2D:
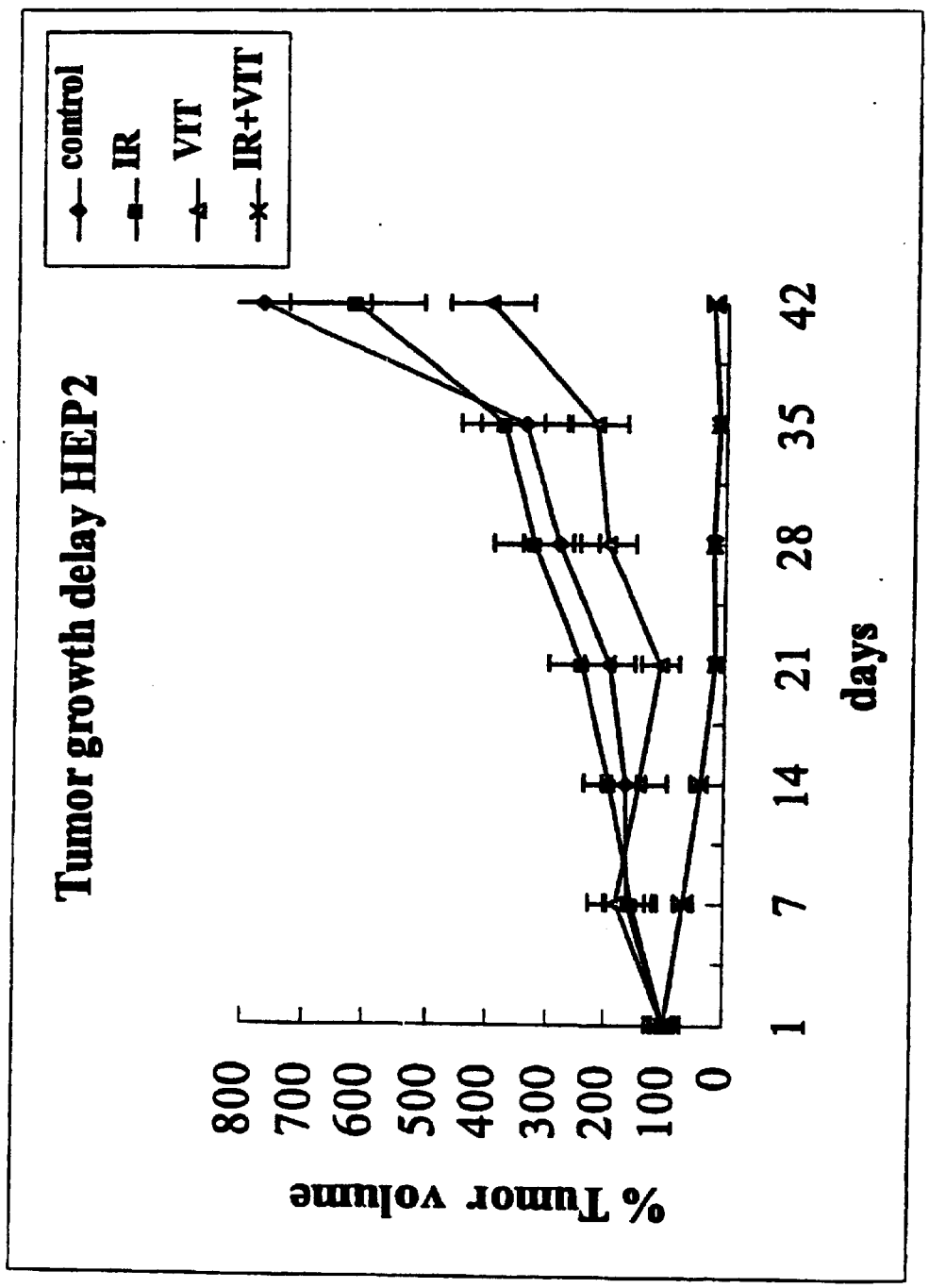
Figure 2E:
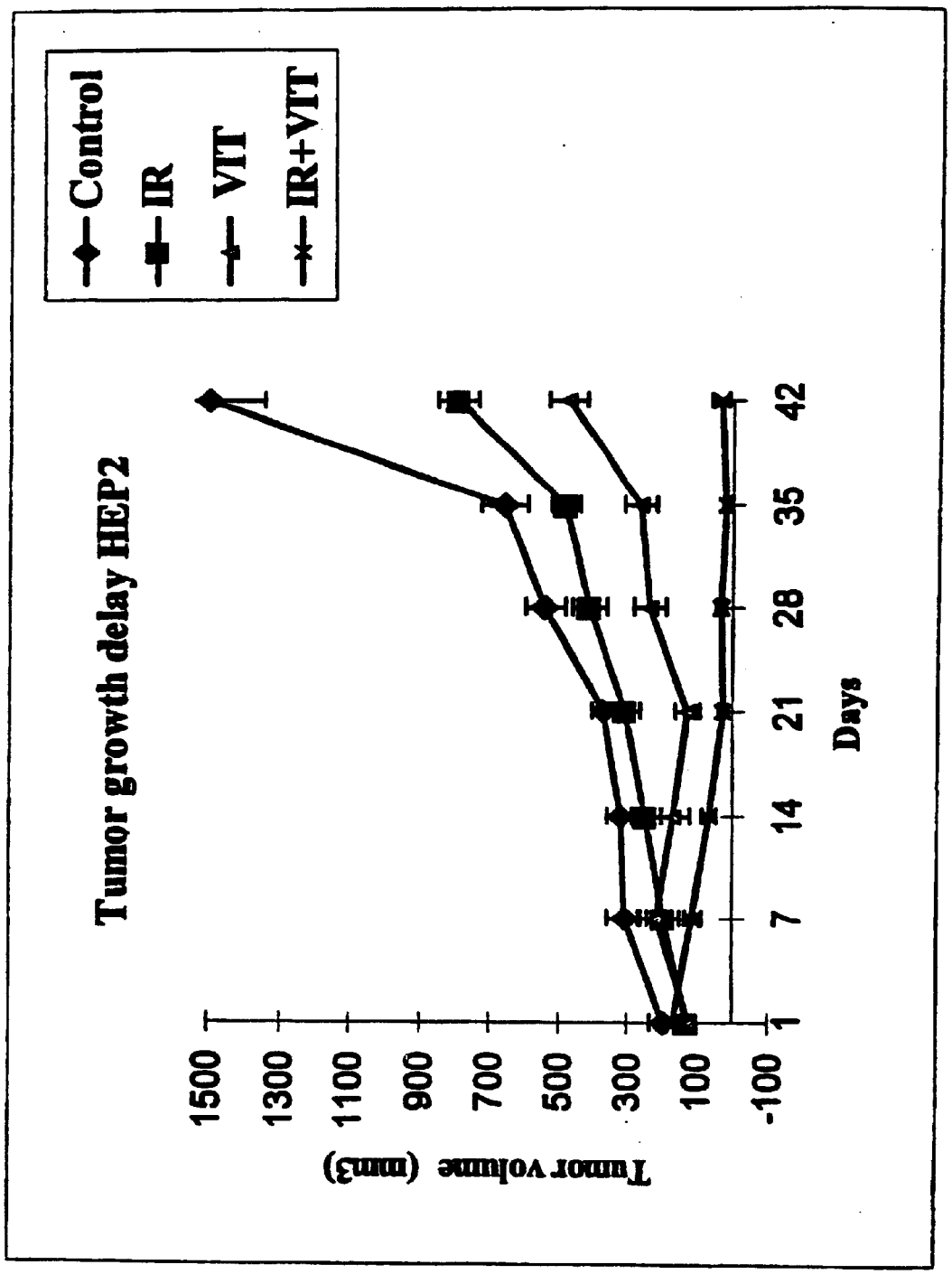

FIG. 1 shows the effect of combining the nucleoside phosphonate HPMPC (Cidofovir), and irradiation on clonogenic cell survival in 3 human cancer cell lines. The effect of the cidofovir alone was substracted for each point measurement. The increased cell kill obtained by the combined treatment was observed both for the virus-related (Raji and HTB33) and for the non-virus-related cancer cells (HTB31).

FIG. 2 shows the effect of the combination of intra-tumor injection of cidofovir and irradiation on tumor growth of several human xenograft cancers in nude mice. The effect is expressed as the % of the initial tumor volume as a function time after the treatment (days). For each cell line, a control group was used as well as a group of irradiation alone (IR), irradiation+cidofovir (IR+VIT), and cidofovir alone (VIT). The results show in all cases a major effect on tumor growth in the group combining the 2 agents (HEP2, HTB33, C15, Raji). For the C15 experiments is also shown the effect of sub-cutaneous injection of 50 mg/kg of cidofovir in combination with irradiation (VSC+IR), showing that intra-tumor and subcutaneous administrations of cidofovir induced, in combination with irradiation, an anti-tumor effect of the same magnitude.

FIG. 3: Proportion of apoptopic cells and LMP-1/Bcl2 expression in EBV+ cells (C15 and RAJI) with and without Cidofovir.

a, RAJI cells were cultured in the presence of Cidofovir (5 and 10 $\mu$g/ml) and irrediated 48 hours later with 3 Gy and then assayed for apoptosis by FACS analysis. C15 tumors were injected intra-tumorally for 5 days with Cidofovir (50 mg/kg/day) and received 7 Gy on day 3 and 5. Animals were sacrified on day 7 and tumors were dissected and prepared for FACS analysis of propidium-iodide nuclei staining as described above.

b, RAJI cells were cultured in the presence or absence of Ciodofovir (10 $\mu$g/ml). At 48 hrs, cells were harvested and analyzed for the expression of LMP1, bcl-2 and bax by Western-blot. For C15, at day 7 portions of tumors where lysed in RIPA buffer and protein extracts were immuno-blotted with anti-LMP-1 antibody. The blot from b was stripped and re-probed with a monoclonal $\beta$-actin antibody. Comparable results were obtained in 3 independent experiments.

Figure 4:
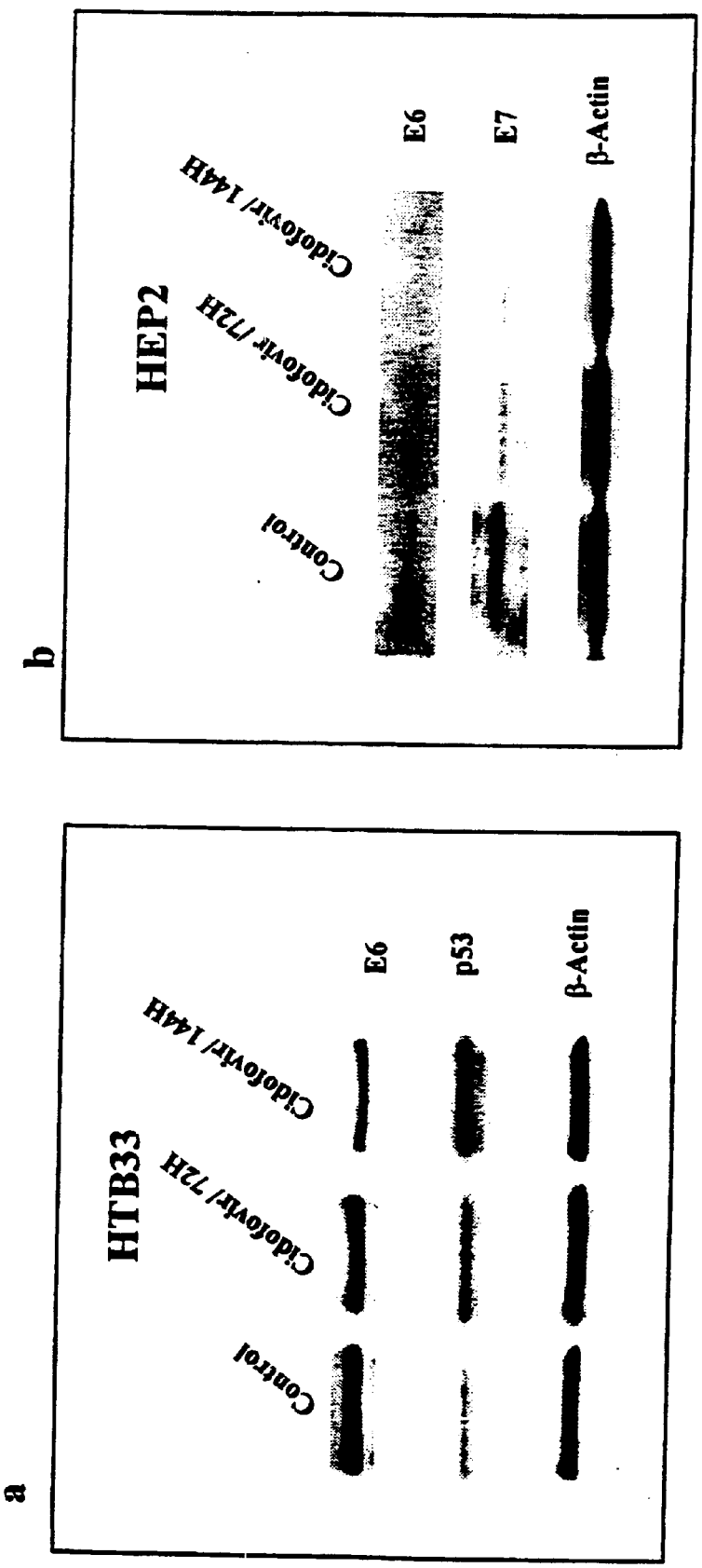

FIG. 4: Viral oncoproteins (E6/E7) and cellular proteins (p53) expression in HPV+HTB33 and HEP2 cells, with and without Cidofovir.

$a_2b_2$ HEP2 (a) and HTB33 (b) cells were cultured in the presence or absence of Cidofovir (10 $\mu$g/ml) for 3 and 6 days, and cells were collected in exponential phase, lysed and total protein were immunoblotted with the Ab-1 anti-E7, C1P5 anti-B6, and DO7 anti-p53. The blots were stripped and re-probed with a monoclonal $\beta$-actin antibody.

Densitometric Analysis of E6 and p53 Bands

HTB33: E6 band was scored 1 without Cidofovir, 0.67 and 0.32, respectively for 3 and 6 days of Cidofovir exposure. P53 density was scored 1 without Cidofovir, 2.1 and 3.7 respectively for 3 and 6 days of Cidofovir exposure.

HEP2: E6 band was scored 1 without Cidofovir, 0.7 and 0.25, respectively for 3 and 6 days of Cidofovir exposure. P53 density was scored 1 without Cidofovir, 1.2 and 1.65 respectively for 3 and 6 days of Cidofovir exposure. Comparable results were obtained in 3 independent experiments.

EXAMPLES

Cell Lines

A typical EBV+ human nasopharyngeal carcinoma cell line like C15 (30) was used in vivo. An EBV+ lymphoma cell lines (Raji) EBV+ and 2 HPV+ squamous cell carcinoma lines, 1 of which originated from the uterine cervix (HTB33) and 1 from the head and neck (HEP2, HPV18+) were used.

A panel of 3 human cancer cell lines from the same tissue origin, but lacking the viral infection were also used; namely 2 HPV-squamous carcinoma cells SCC97 (head and neck), HTB31 (cervix) and the EBV-Ramos lymphoma cells.

Cell lines Raji (CCL-86), Ramos (CRL-1596), Hep2 (CCL-23), C33A (HTB-31) and Me-180 (HTB-33) are available in the ATCC (American Type Culture Collection) catalogue.

Cells were grown in MEM medium supplemented with 15% fetal calf serum, penicillin/streptomycin and 2 mM glutamine at 5% CO2.

Apoptosis Assay

The cell cycle distribution was estimated by staining ethanol-fixed cells with propidium iodide and monitoring by FACScan flow cytometer (Becton Dickinson) using cellQuest software. Briefly, $1 \times 10^6$ cells were cultured without or with 5 and 10 µg/ml of Cidofovir, 24 hours later cells were irradiated with 3 and 6 Gy and collected 12 and 24 hours after irradiation. The percentage of apoptotic cells was determined by sub-G1 peak.

Histological Sections

At 10 day after treatment, mice with HPV+ tumors from all groups were sacrified and tumors were excised and fixed in 10% neutral buffered formalin (NBF). The sections from each group were heamatoxylin and eosin (H&E)-stained for histological analysis.

Immunoblot Analysis

To prepare total proteins, cells lysates were extracted with lysis buffer 50 mM tris, pH 8, 120 mM NaCl, 0,1% SDS, and 0,5% NP-40. The protein concentration in the soluble fraction was determined by using a BioRad protein assay reagent. The viral oncoprotein LMP1 was detected by immunoblotting with a monoclonal anti-LMP1 antibody (clone CS1,CS2,CS3 & CS4 cocktail, RDI). The following antibodies were used: anti-Bcl2 (clone 100 Santa Cruz Biotechnology), anti-Bax (clone B-9, Santa Cruz, anti-E6 (clone CIP5, abcam), anti-E7 (clone Ab-1, oncogene), anti-p53 (clone DO7, Dako). Anti β-actin (clone AC-40, Sigma) was used to control protein loading. Autoradiograms of the Western blot were scanned with the Gil doc 1000 image scanner (Bio-rad, Hercules, Calif.) and densitometric analysis of the bands was performed using the molecular analyst software program (Bio-rad, Hercules, Calif.).

Statistical Analysis

In vivo data are reported as the percentage of original (day 0) tumor volume and plotted as fractional tumor volume±S.E. Statistical significance was determined by Kruskal/Wallis and Mann-Withney U tests.

In vivo Experiments

Female Swiss nu/nu mice were housed throughout experiments in sterile isolators and fed ad libitum with irradiated food (UAR, Villemoisson/Orge, France) and filtered water. Experiments were performed according to the regulation n°86/609/CEE of the European Community. Cell lines were established in vivo in Swiss athymic mice by subcutaneous injection in the right flank of $5 \times 10^6$ cells per animal and subsequently maintained in vivo by sequential passages in animals aged 6 to 8 weeks. Nude mice bearing 500–1000 mm3 tumors were used for in vivo experiments. Two types of control were used including both injection of PBS (intratumor and intravenous (IV)), irradiation alone, or chemotherapy alone.

Irradiation and Clonogenic Survival Assay.

Irradiation of cells was performed using a $^{137}$Cs γ-rays source at a dose rate of 1.45 Gy.min$^{-1}$. Briefly survival curves were obtained by irradiating cells (0 to 6 Gy). The linear-quadratic model was used for fitting survival curves. Quantification of radiosensitivity was obtained by the surviving fraction at 2 Gy (SF2). Cell survival was also assessed by using proliferation tests (incorporation of tritiated thymidine and MTT). Irradiation of animals was performed using a 200 kv apparatus.

Molecular Basis of the Invention

This aspect was mainly studied using western immunoblots and flow cytometry (FACS) for protein expression analysis and protein co-precipitation analysis (immunoprecipitation).

The Combination of Cidofovir and Ionizing Radiation Increases Apoptosis and Tumor Necrosis.

Figure 3A:
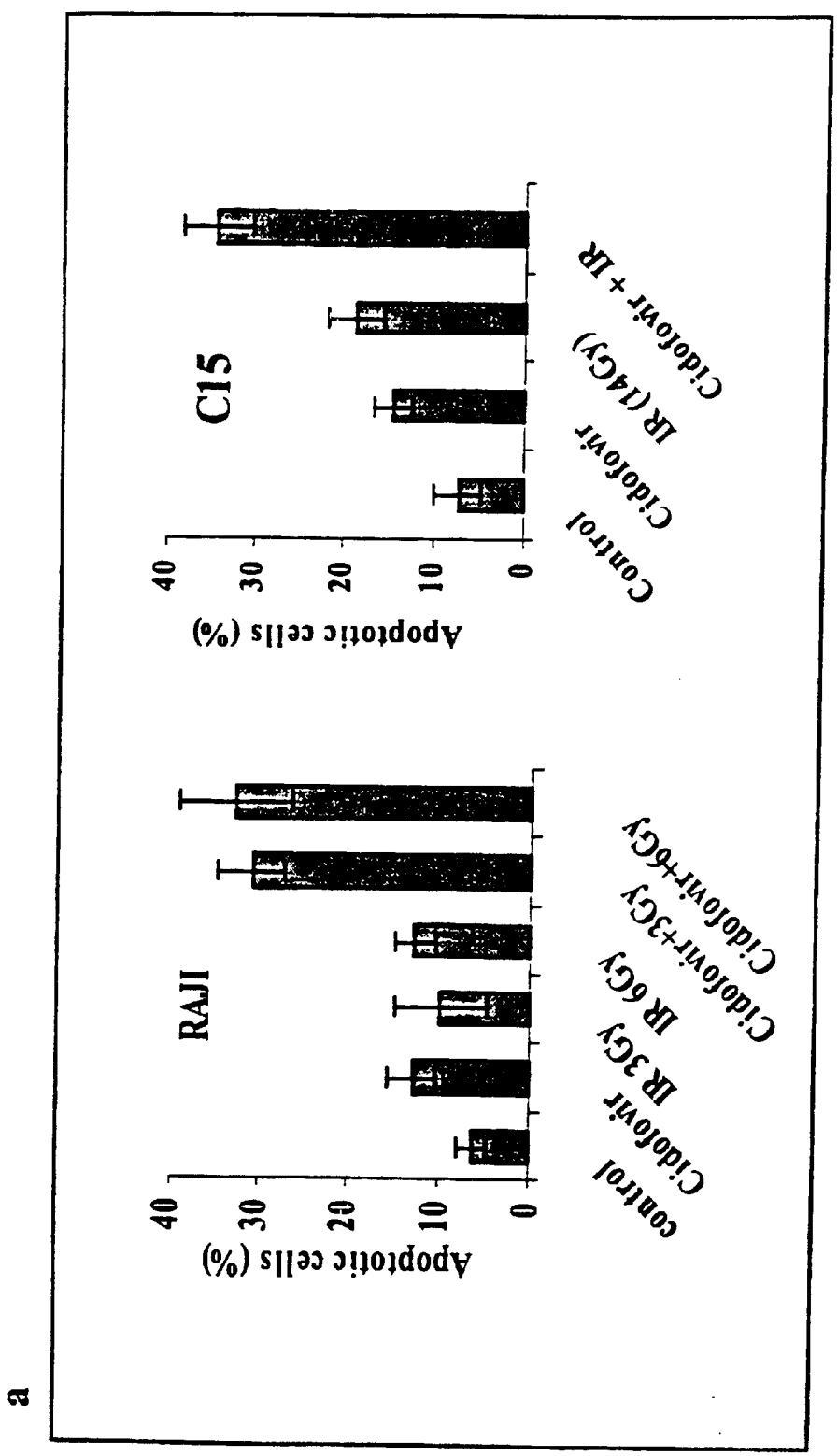

Cidofovir is a potent inhibitor of the replication of EBV and HPV in cell culture. In addition, the incorporation into the cellular DNA of the infected cell may disrupt the genomic integrity and enhance susceptibility to apoptosis or necrosis. In C15 and RAJI cell lines, Cidofovir (10 µg/ml) combined with irradiation (3 and 6 Gy) induced a marked increase of apoptosis (FIG. 3a). The histological sections showed that increased tumor necrosis was predominantly seen in the 2 HPV+ models (data not shown). Both in EBV and HPV cancer cells, no significant change in radiation-induced DNA repair was observed, as measured at the chromosomal level by Fluorescence In Situ Hybridization (FISH) (data not shown).

Cidofovir Induces a Modulation of Some Viral Oncoproteins.

The effect of the combined treatment was major in the EBV+ and HPV+ cancer cells, whereas it was relatively marginal in the corresponding virus negative models, suggesting a potential role for some viral oncoproteins in this process (FIG. 1). Indeed, the transforming properties of the EBV and HPVs are attributed to the interaction of viral oncoproteins with critical cellular proteins that control cell proliferation and apoptosis cell death (31,32). Gene-transfer experiments have shown that the expression of LMP-1 specifically inhibits p53-mediated apoptosis, by inducing the antiapoptotic cellular genes, Bcl-2 and A20.

Figure 3B:
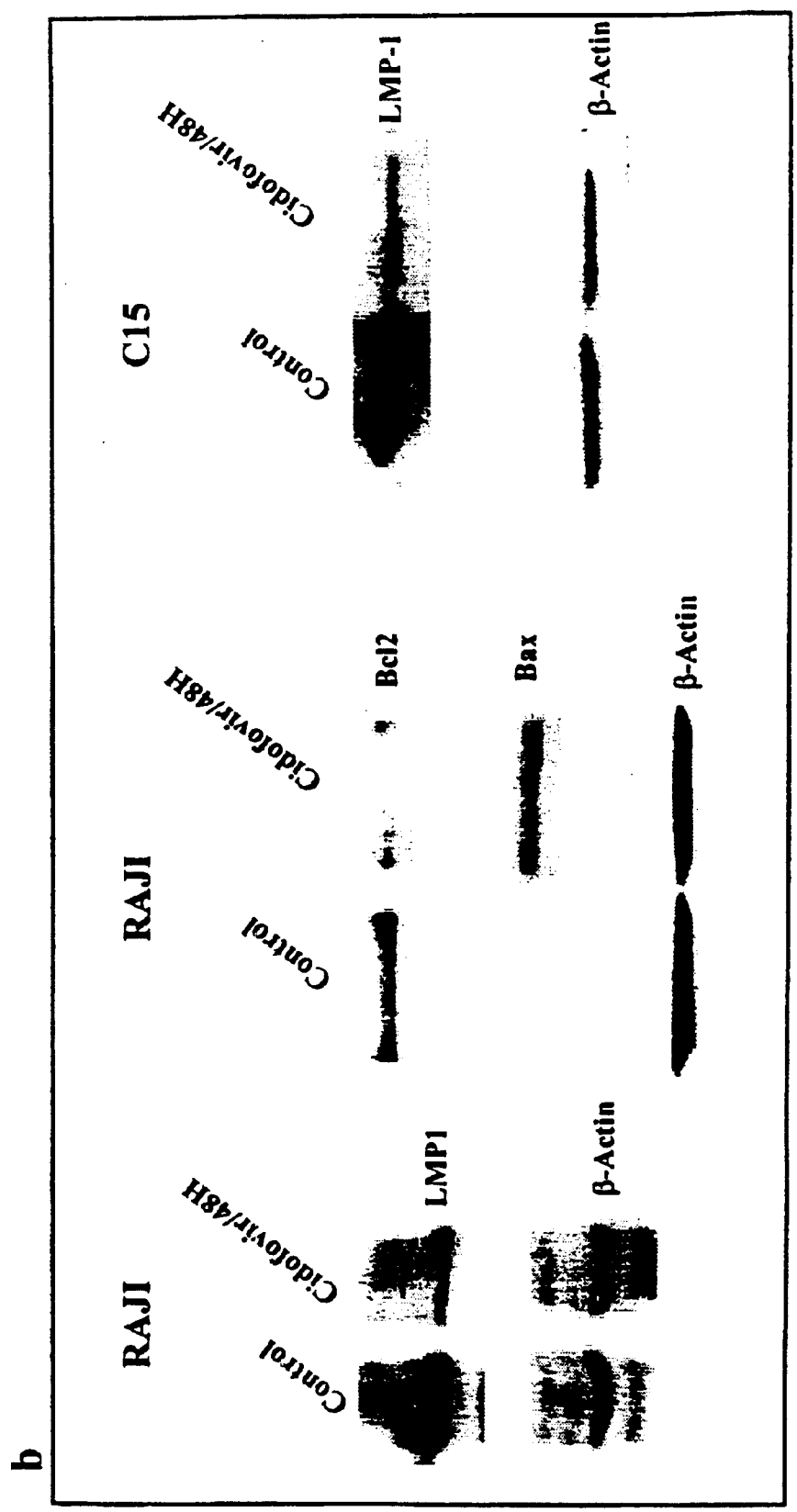

Cidofovir exposure was able to induce a marked decrease of LMP-1 expression both in RAJI and C15 cells (FIG. 3b). We observed significant inhibition of LMP-1 expression as early as 24 hours (data not shown) and more pronounced inhibition 48 hours after exposure to Cidofovir (FIG. 3b). The result might be related to the inhibition of the viral replication and it is compatible with the short half-life of LMP-1 protein (33). Importantly, the inhibition of LMP-1 was associated with a downregulation of the LMP-1 inducible gene Bcl2, an up-regulation of the pro-apoptotic Bax expression (FIG. 3b). In latent EBV infection as it occurs in C15 an RAJI cells, the induction of antiapoptotic genes by LMP-1 presumably contributes to protect cells from apoptosis (31). Such a down regulation of LMP-1 and Bcl2 by Cidofovir could explain the enhancement of the sensitivity to readiation-induced apoptosis observed in the FBV+ cell lines (RAJI and C15). Downregulation of LMP-1 is reported here for the first time in cancer cells using a pharmacological approach.

E6 and E7 oncoproteins are involved in cellular transformation by interacting with the tumor suppressor proteins Rb and p53, respectively (34, 35). P53 functional assay in yeast (36) showed that p53 gene was wild type in cervical carcinoma HTB33 and head and neck HEP2 cells (data not shown). However, the basal level of p53 expression was relatively low as shown in FIG. 4a, and a previously reported (35) which is compatible with a proteasome-mediated degradation of p53 by E6 oncoprotein expressed in these two cell lines. Unlike other cancers in which p53 is mutated, the notion has arisen that the effect of E6 with respect to p53 is equivalent to an inactivating mutation of p53 (32). This underlines the importance of targeting E6 for therapeutic intervention since blocking E6-mediated degradation of p53 may be efficient to restore a normal p53 expression in HPV1 cells (32). In this study, we showed that Cidofovir exposure was able to down-regulate E6 expression with subsequent increase of p53 expression (FIG. 4a, 4b). This phenomenon was likely to enhance the sensitivity to ionising radiation since the restoration of a normal wtp53 expression has been shown to increase the radiosensitivity in many human carcinoma models (37,38). In addition, a decreased expression of the viral oncoprotein E7 was observed when these HPV+ cells were exposed to Cidofovir (FIG. 4b). It is important to point out that Cidofovir was able to influence both E6 and E7 expression which may be more efficient for growth suppression than targeting each of these proteins separately (39).

Conversely, recent data have shown that E6/E7 viral oncoproteins overexpression was associated to p53 down-regulation and radiation induced apoptosis inhibition in cervical carcinoma cell line (40).

Some Examples of Interaction Between the Acyclic Nucleoside Phosphonate Analogues and Cytotoxic Agents are Presented Herewith:

Example N°1

Combination of an Acyclic Nucleoside Phosphonate Analogue with Irradiation in Human Cancer Cells in vitro The example presented herewith relates to the combination of cidofovir with irradiation, which was evaluated in vitro in various virus-related and non virus-related human cancers.

It was studied in EBV+ human carcinoma C15 cells, EBV+ lymphoma Raji cells, 2 HPV+ carcinoma HTB33 and HEP2 cells. The effect of the combination was also studied in 3 human cell lines lacking the viral infection namely Ramos (lymphoma) HTB31 and SCC97 (carcinoma) cells.

For each cell line, several concentrations of cidofovir were used in vitro in combination with irradiation (between 1 and 10 $\mu$g/ml). The effect of the combined treatment was evaluated using both a proliferation test and a clonogenic assay for cell survival. These two methods gave convergent results showing in all the EBV+ and HPV+ cell lines, that the addition of cidofovir to irradiation produced a pronounced radiosensitization as shown by the dramatic decrease of the SF2 (surviving fraction at 2 Gy). This marked radiosensitizing effect was not restricted to the cell lines exhibiting a viral infection since non virus-containing cells Ramos, HTB31, and SCC97 were also markedly radiosensitized by the cidofovir (see examples in FIG. 1).

Example N°2

Combination of an Acyclic Nucleoside Phosphonate Analogue with Irradiation in Human Cancer Xenografts in vivo The example presented herewith also relates to the combination of cidofovir with irradiation which was evaluated in vivo in various human viral-associated and also in non viral associated human cancers. The effect of cidofovir alone or combined with irradiation was studied in vivo in nude mice bearing 500–1000 mm3 tumor xenografts. The treatment consisted of 60 mg/kg daily of cidofovir intra-tumor injection for 5 days. In the combined group, irradiation (7 Gy) was performed on day 3 and 5 of cidofovir. As shown in FIG. 2; both irradiation alone and cidofovir alone induced a weak growth delay, whereas the concomitant association of both agents dramatically reduced the growth delay for the virus-positive tumors (C15, Raji, HEP2, HTB33 . . . ), as well as for the non-virally induced tumors tested. In all cases, in the group receiving the combined treatment, nearly all the tumors were found to be in complete remission, 30 to 40 days after the treatment, suggesting the existence of a major interaction between the 2 agents.

Effect of the Route of Administration in vivo:

In vivo, the effect of non toxic doses 25 to 75 mg/kg from day 1 to day 5 of the nucleoside phosphonate analogues administered intra-peritoneally or subcutaneously (C15, HTB33 etc . . . ) was found to be as efficient for tumor inhibition (FIG. 2), as compared to the intra-tumor mode of administration. The doses used intra-peritoneally and subcutaneously were in the range of 0.5 to 1.66 times the doses used for intra-tumor injections.

Molecular Basis of the Observed Effect

The molecular basis of the interaction is not fully understood. In the non-virus related cancer types, nucleoside phosphonate analogue were found to interfere with DNA repair, apoptosis and cell cycle regulation (cyclin D1, E and A), which could explain the observed radiosensitization. In addition to these mechanisms, in the virus-associated cancer types, an inhibition of the viral oncoproteins could be also observed. For example, in the EBV+ raji cells, nucleoside phosphonate analogues induced a down regulation of the viral oncoprotein LMP1 and consequently the anti-apoptotic Bcl2 gene expression was down regulated, contributing to increase radio-induced tumor cell kill.

In conclusion, the combination of an anti-viral nucleoside phosphate analogue and irradiation described in this example represents a totally new approach for the treatment of virus-associated and non-virus-associated human cancers. Indeed, the results obtained showed a major effect of combining this type of anti-viral agent with irradiation.

Example N°3

Combination of an Acyclic Nucleoside Phosphonate Analogue with Chemotherapeutic Agents in Human Cancer Cells Similar experiments combining a nucleoside analogue with cytotoxic agents other than irradiation were performed (chemotherapeutic drugs, cytokines). The example presented herewith relates to the combination of cidofovir with chemotherapeutic drugs which was evaluated in vitro and in vivo in various virus-associated and non virus-associated human cancers. Two drugs were tested, showing a synergic inhibitory effect on tumor cell growth using a combination of a nucleoside phosphonate analogue with cis platinum (2.5 $\mu$g/ml, in vitro) and VP16 (5 $\mu$g/ml, vitro).

REFERENCES

1. Andrei G, Snoeck R, Piette J, Delvenne P, De Clercq E. Inhibiting effects of cidofovir (HPMPC) on the growth of the human cervical carcinoma (SiHa) xenografts in athymic nude mice. Oncol Res 1998;10(10):533–9.
2. Andrei G, Snoeck R, Piette J, Delvenne P. De Clercq E. Antiproliferative effects of acyclic nucleoside phosphonates on human papillomavirus (HPV)-harboring cell lines compared with HPV-negative cell lines. Oncol Res 1998;10(10):523–31.
3. Johnson J A, Gangemi J. Selective inhibition of human papillomavirus-induced cell proliferation by (S)-1-[3-hydroxy-2-(phosphonylmethoxy)propyl]cytosine. Antimicrob Agents Chemother 1999 May;43(5):1198–205.

4. Petersen B L, Buchwald C, Gerstoft J, Bretlau P, Lindeberg. An aggressive and invasive growth of juvenile papillomas involving the total respiratory tract. J Laryngol Otol 1998 November;112(11):1101–4.
5. Boulanger Human herpesvirus 8 (HHV8). II. Pathogenic role and sensitivity to antiviral drugs. Ann Biol Clin (Paris) 1999 January–February;57(1):19–28.
6. Simonart T, Noel J C, De Clercq E, Snoeck. Abatement of cutaneous Kaposi's sarcoma associated with cidofovir treatment. Clin Infect Dis 1998 December;27(6):1562.
7. Badiaga S, Parola P, Zandotti C, Brouqui. Successful treatment of Kaposi's sarcoma with a combination of anti-viral drug therapy and chemotherapy: two case reports. Clin Infect Dis 1998 December;27(6):1558–9.
8. Arribas J R, Arrizabalaga J, Mallolas J, Lopez-Cortes L. Advances in the diagnosis and treatment of infections caused by herpesvirus and JC virus. Enferm Infect Microbiol Clin 1998;16 Suppl 1:11–9.
9. Zabawski E J Jr, Cockerell C J. Topical and intralesional cidofovir: a review of pharmacology and therapeutic effects. J Am Acad Dermatol 1998 November;39 (5 Pt 1): 741–5.
10. Gross G. Therapy of human papillomavirus infection and associated epithelial tumours. Intervirology 1997;40 (5–6):368–77.
11. Liekens S, Andrei G, Vandeputte M, De Clercq E, Neyts J. Potent inhibition of hemangioma formation in rats by the acyclic nucleoside phosphonate analogue cidofovir. Cancer Res Jun. 15, 1998;58(12):2562–7
12. Simonart T, Noel J C, De Dobbeleer G, Parent D, Van Vooren J P, De Clercq E, Snoeck. Treatment of classical Kaposi's sarcoma with intralesional injections of cidofovir: report of a case. J Med Virol 1998 July;55(3):215–8
13. Hammoud Z, Parenti D M, Simon G. Abatement of cutaneous Kaposi's sarcoma associated with cidofovir treatment. Clin Infect Dis 1998 May;26(5):1233.
14. Snoeck R, Wellens W, Desloovere C, Van Ranst M, Naesens L, De Clercq E, Feenstra L. Treatment of severe laryngeal papillomatosis with intralesional injections of cidofovir [(S)-1-(3-hydroxy-2-phosphonylmethoxypropyl)cytosine]. J Med Virol 1998 March;54(3):219–25.
15. LoPresti A E, Levine J F, Munk G B, Tai C Y, Mendel D. Successful treatment of an acyclovir- and foscarnet-resistant herpes simplex virus type 1 lesion with intravenous cidofovir. Clin Infect Dis 1998 February;26(2):512–3.
16. Neyts J, Sadler R, De Clercq E, Raab-Traub N, Pagano J. The anti-viral agent cidofovir [(S)-1-(3-hydroxy-2-phosphonyl-methoxypropyl)cytosine] has pronounced activity against nasopharyngeal carcinoma grown in nude mice. Cancer Res Feb. 1, 1998;58(3):384–8.
17. Zabawski E J Jr, Sands B, Goetz D, Naylor M, Cockerell C. Treatment of verruca vulgaris with topical cidofovir. JAMA Oct. 15, 1997;278(15):1236.
18. Medveczky M M, Horvath E, Lund T, Medveczky P. In vitro anti-viral drug sensitivity of the Kaposi's sarcoma-associated herpesvirus. AIDS 1997 September;11 (11):1327–32.
19. Kedes D H, Ganem D. Sensitivity of Kaposi's sarcoma-associated herpesvirus replication to anti-viral drugs. Implications for potential therapy. J Clin Invest May 1, 1997;99(9):2082–6.
20. Baker G E, Tyring S. Therapeutic approaches to papillomavirus infections. Dermatol Clin 1997 April;15(2):331–40.
21. de Oliveira C B, Stevenson D, LaBree L, McDonnell P J, Trousdale M. Evaluation of Cidofovir (HPMPC, GS-504) against adenovirus type 5 infection in vitro and in a New Zealand rabbit ocular model. Anti-viral Res 1996 July;31(3):165–72.
22. Van Cutsem E, Snoeck R, Van Ranst M, Fiten P, Opdenakker G, Geboes K, Janssens J, Rutgeerts P, Vantrappen G, de Clercq E, et al. Successful treatment of a squamous papilloma of the hypopharynx-esophagus by local injections of (S)-1-(3-hydroxy-2-phosphonylmethoxypropyl)cytosine. J Med Virol 1995 February;45(2):230–5.
23. Snoeck R, Andrei G, Gerard M, Silverman A, Hedderman A, Balzarini J, Sadzot-Delvaux C, Tricot G, Clumeck N, De Clercq E. Successful treatment of progressive mucocutaneous infection due to acyclovir- and foscarnet-resistant herpes simplex virus with (S)-1-(3-hydroxy-2-phosphonylmethoxypropyl)cytosine (HPMPC). Clin Infect Dis 1994 April;18(4):570–8.
24. Connelly M C, Robbins B L, Fridland A. Mechanism of uptake of the phosphonate analog (S)-1-(3-hydroxy-2-phosphonylmethoxypropyl)cytosine (HPMPC) in Vero cells. Biochem Pharmacol Sep. 14, 1993;46(6):1053–7.
25. Neyts J, Snoeck R, Balzarini J, De Clercq E. Particular characteristics of the antihuman cytomegalovirus activity of (S)-1-(3-hydroxy-2phosphonylmethoxypropyl)cytosine (HPMPC) in vitro. Anti-viral Res 1991 July;16 (1):41–52.
26. Bourhis J., Cvitcovic E, Eschwege F. O'Malley B. Nasopharyngeal carcinoma. In: Head and neck: a multi-disciplinary approach. Harrison L., Roy B., Hong W. K., eds. Lippincott-Raven publishers, pp 639–667, 1998.
27. Howley P., Principle of carcinogenesis: viral. In V; T DeVita, S Hellman, A Rosenberg, eds Principle and practice in Oncology. $4^{th}$ Edition, pp 182–95, 1993.
28. De Clerck E., Andrei G., Balzani J., Hatse S., Liekens S., Naesens L., Neyts J., Snoeck R. Antitumor potential of acyclic nucleoside phosphonates. Nucleosides Nucleotides 18: 759–71, 1999.
29. De Clercq E. Toward an effective chemotherapy of virus infection: therapeutic potential of cidofovir (S-1-(3-hydroxy-2-phosphonomethoxy)propyl) cytosine, HPMPC, for the treatment of DNA virus infections. Collect. Czech. Commun, 63: 1998.
30. Busson et al, Int. J. Cancer, 42, 599–606, 1988.
31. Kaye, et al, Epstein-Barr virus latent membrane protein 1 is essential for B-lymphocyte growth transformation. Proc. Natl. Acad. Sci. USA, 90:9150–9154, 1993.
32. Thomas, et al. The role of the E6-p53 interact on in the molecular pathogenesis of HPV. Oncogene., 18: 7690–7700, 1999.
33. Baichwal, V R., and Sugden, B., Posttranslational processing of an Epstein-Barr virus-encoded membrane protein expressed in cells transformed by Epstein-Barr virus. J. Virol., 61 (3): 866–75, 1987.
34. Dyson, N. et al. The human papillomavirus-16 E7 oncoprotein is able to bind to the retinoblastoma gene product. Science, 243: 934–937, 1989.
35. Mietz, J A., et al. The transcriptional transactivation function of wild-type p53 is inhibited by SV40 large T-antigen and by HPV-16 E6 oncoprotein EMBO J; 11: 5013–5020, 1992.
36. Flaman, J M., et al, A simple p53 functional assay for screening cell lines, blood, and tumors. Proc. Natl. Acad. Sci USA, 92: 3963–3967, 1995.
37. Gallardo, D., et al. Adenovirus-based transfer of wild-type p53 gene increases ovarian tumor radiosensitivity. Cancer Res. 56: 4891–4903, 1996.
38. Spitz, F R., et al., Adenoviral mediated p53 gene therapy enhances radiation sensitivity of colorectal cancer cell lines. Clin Cancer Res. 2: 1665–1671, 1996.

39. Francis, D A. Et al, Repression of the integrated papillomavirus E6/E7 promoter is required for growth suppression of cervical cancer cells. J. Virol. 74: 2679–2686, 2000.
40. Kamradt, M C., Inhibition of radiation-induced apoptosis by dexamethasone in cervical carcinoma cell lines depends up in increased HPVE6/E7. Br J Cancer., 82: 1709–1716, 2000.

What is claimed is:

1. A method of treating a virus-associated cancer comprising: administering to an individual an antiviral agent and an anti-cancer treatment, wherein said administration of both said antiviral agent and said anti-cancer treatment results in a synergistic effect and wherein the antiviral agent is HPMPC [(S)-1-[3-hydroxy-2-(phosphomethoxy)propyl] cytosine] and the anticancer treatment is radiotherapy.

2. A method of treating a lymphoma or a carcinoma, comprising: administering to an individual an antiviral agent and an anti-cancer treatment, wherein said administration of both said antiviral agent and said anti-cancer treatment results in a synergistic effect.

3. A method according to claim 1 or 2, wherein the antiviral agent is administered systematically, parenterally, intratumorly or topically.

4. A method according to claim 1 or 2, wherein the antiviral agent is administered at a nontoxic dose.

5. A method according to claim 2, wherein the lymphoma or carcinoma is a non-virus associated cancer.

6. A method according to claim 1, wherein the viral-associated cancer is associated with an infection by a virus chosen among herpes-, adeno-, polyoma-, papilloma-, Epstein-Barr or Hepatitis DNA viruses.

7. A method according to claim 1, wherein the cancer is a virus-associated cancer involving infection by EBV or HPV virus.

* * * * *